United States Patent
Keller

(10) Patent No.: US 8,038,651 B2
(45) Date of Patent: Oct. 18, 2011

(54) DEVICE WITH PRESSURE-ACTUATED PISTONS FOR DISPENSING A MULTIPLE SYRINGE OR MULTIPLE CARTRIDGE

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 86 days.

(21) Appl. No.: 12/320,343

(22) Filed: Jan. 23, 2009

(65) Prior Publication Data
US 2009/0192460 A1   Jul. 30, 2009

(30) Foreign Application Priority Data
Jan. 29, 2008   (CH) ........................................ 0124/08

(51) Int. Cl.
*A61M 5/20*   (2006.01)
(52) U.S. Cl. ........................................ 604/136; 604/131
(58) Field of Classification Search .......... 604/134–136, 604/82–92, 232–234, 157, 131
See application file for complete search history.

(56) References Cited

U.S. PATENT DOCUMENTS

| | | |
|---|---|---|
| 2,565,081 A | 8/1951 | Maynes |
| 3,702,608 A | 11/1972 | Tibbs |
| 3,702,609 A | 11/1972 | Steiner |
| 5,584,815 A * | 12/1996 | Pawelka et al. ............... 604/191 |
| 5,722,956 A * | 3/1998 | Sims et al. .................... 604/131 |
| 5,891,086 A | 4/1999 | Weston |
| 6,228,067 B1 | 5/2001 | Gabriel |
| 6,544,234 B1 | 4/2003 | Gabriel |
| 6,802,822 B1 * | 10/2004 | Dodge ............................ 604/82 |

FOREIGN PATENT DOCUMENTS

| | | |
|---|---|---|
| DE | 1 957 833 | 7/1970 |
| DE | 200 06 986 | 7/2000 |
| DE | 10 2005 048 871 | 4/2007 |
| WO | WO-95/03844 | 2/1995 |
| WO | WO-99/37343 | 7/1999 |

OTHER PUBLICATIONS

European Search Report Issued for Application No. EP 09 40 5004, 4 pages.

* cited by examiner

*Primary Examiner* — Nicholas D Lucchesi
*Assistant Examiner* — Melissa A Snyder
(74) *Attorney, Agent, or Firm* — Foley & Lardner LLP

(57) ABSTRACT

The suggested device comprises a dispensing piston that is actuatable by a pressure medium for dispensing a syringe and a guide portion within which the dispensing piston is displaceably supported. The device is designed for dispensing a double syringe and includes a handling portion for receiving the pressure medium, the dispensing piston, and the guide portion, as well as locking means that are releasable by applying manual pressure to the handling portion and are arranged on the handling portion and operatively connected to locking means provided on the dispensing piston. This allows a very simple repeated use of this arrangement for self-dispensing by patients, and remote wounds, e.g. an arm or foot wound, can also be treated by the patient independently.

15 Claims, 4 Drawing Sheets

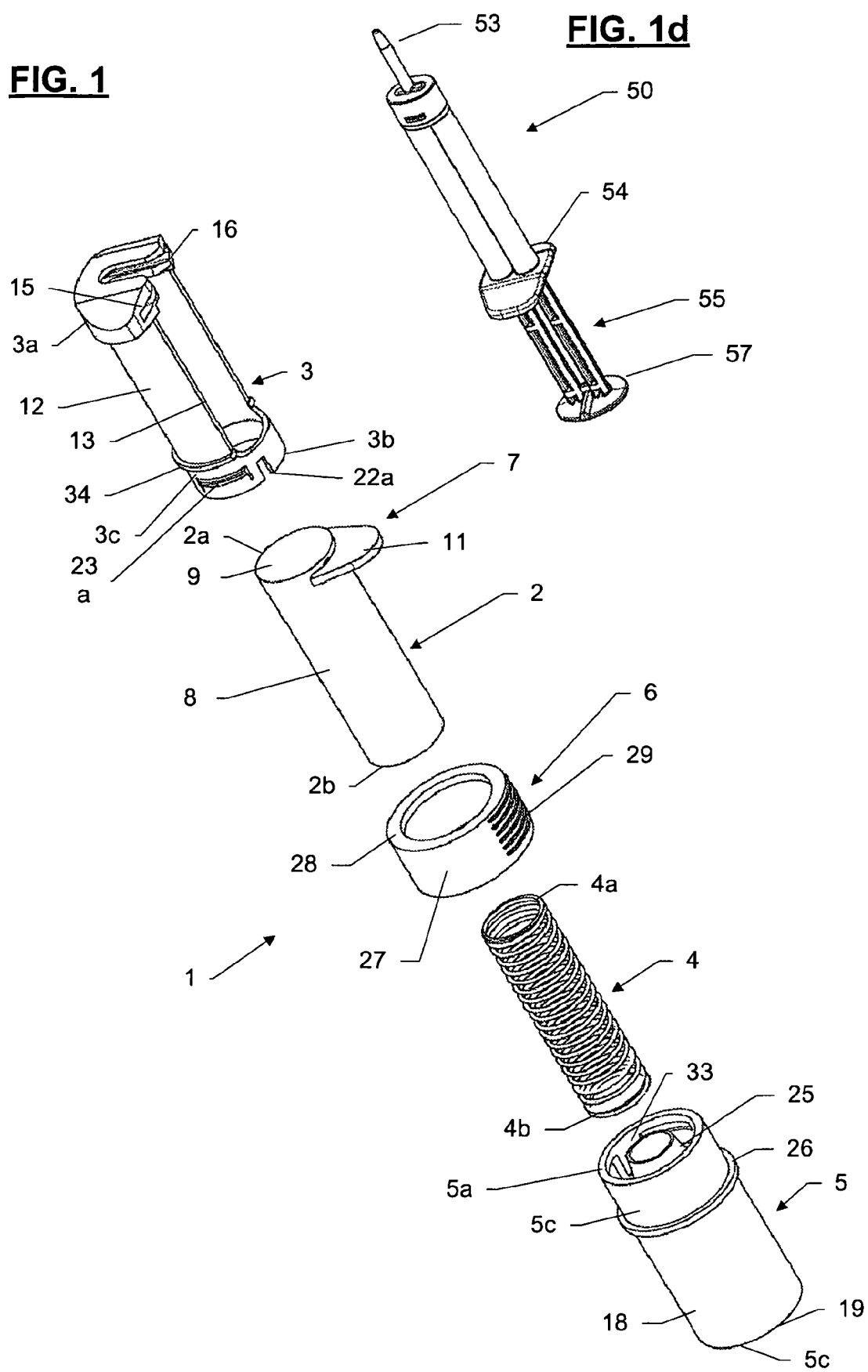

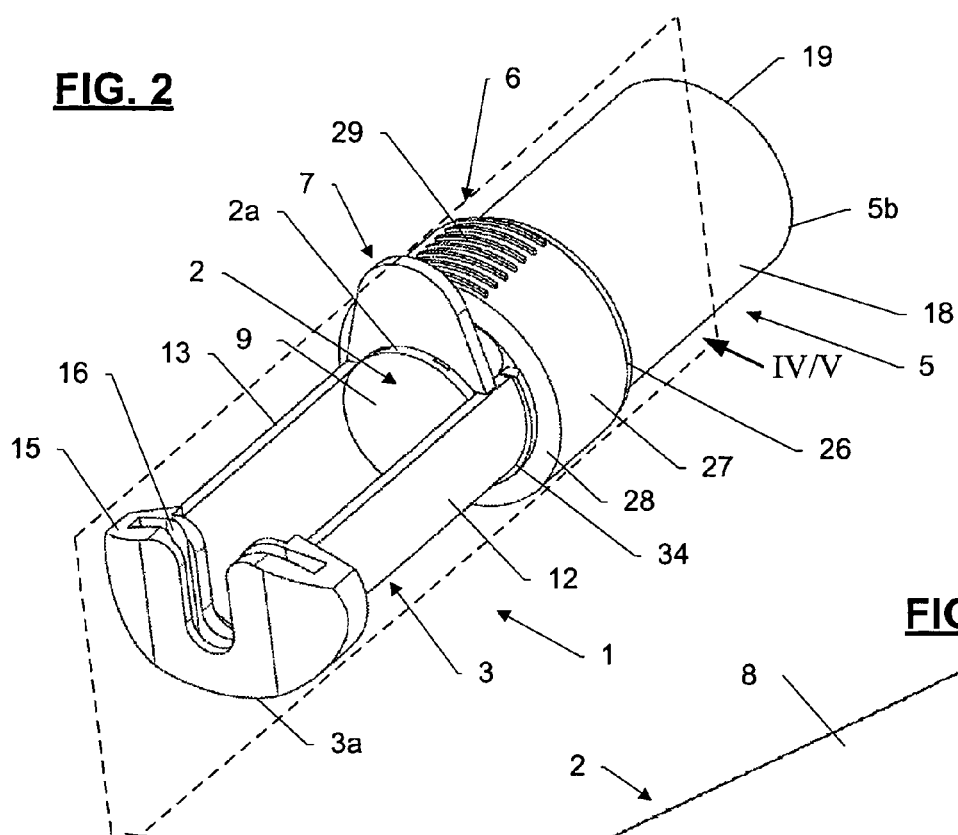
FIG. 2
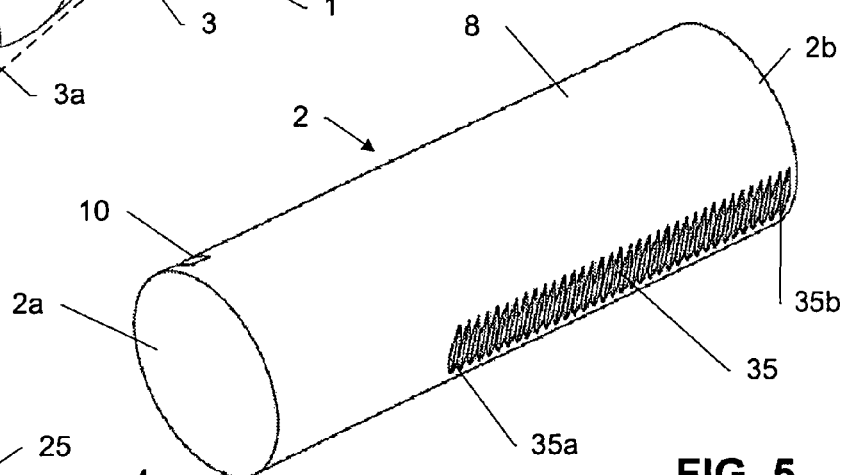
FIG. 3
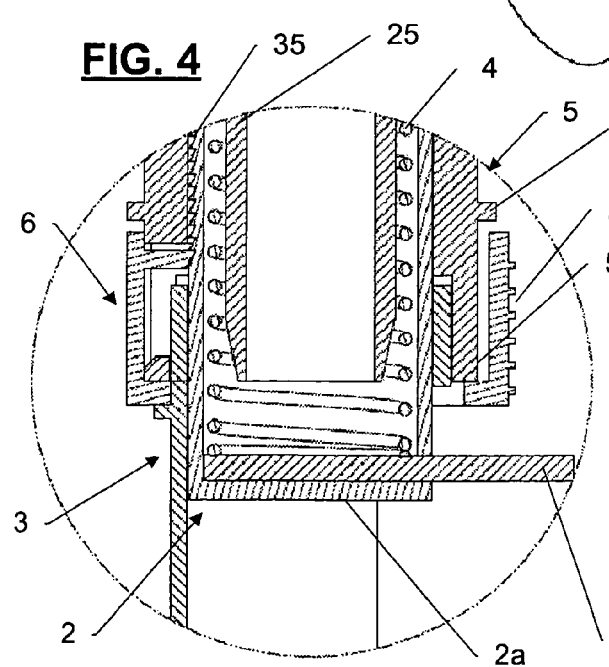
FIG. 4
FIG. 5

DEVICE WITH PRESSURE-ACTUATED PISTONS FOR DISPENSING A MULTIPLE SYRINGE OR MULTIPLE CARTRIDGE

BACKGROUND OF THE INVENTION

The invention relates to a device having a dispensing piston that is actuatable by a pressure medium for dispensing a syringe and a guide portion within which the dispensing piston is displaceably supported.

A dispensing syringe of this kind with a hypodermic needle is known from U.S. Pat. No. 2,565,081 where the device comprises an actuator that is actuatable by a compression spring and a guide portion within which the dispensing plunger is displaceable. The actuator is held in its tensioned position by a locking catch at its rear end and pressed onto the plunger of the syringe when the locking catch is released. During this operation, the spring expands once.

U.S. Pat. No. 3,702,608 discloses a dispensing assembly having a portion for receiving a single syringe at its end opposite the outlet and a relatively complicated dispensing mechanism.

WO 99/37343 also discloses a dispensing assembly that is capable of receiving a single syringe and has a relatively complicated releasing mechanism.

In the field of wound treatment, besides conventional dressing materials for sterile wound coverage, liquids, pastes, and gelatin are also used which in combination with other substances allow sealing and healing of wounds and pain relief. For this purpose, multicomponent substances are increasingly being used which, however, have to be combined and mixed prior to their application to the wound. To this end, the components are e.g. stored in a double syringe and mixed by means of a static mixer or a spray system prior to their application to the skin or wound surface. Dispensing of the mixture is achieved by applying manual pressure to the plunger of the double syringe.

Particularly for long-term patients or in the case of chronic wounds, an autonomous wound treatment by the patient is not only desirable but also cost-saving. However, in a conventional double syringe, the dispensing operation requires a force and a certain manual ability of the patient that should not be underestimated. Depending on the location of the wound, it may be difficult for the patient to operate the double syringe.

Furthermore, a possibility of metering the components to be dispensed is desirable, which is only insufficiently ensured by conventional double syringes.

SUMMARY OF THE INVENTION

On this background, the invention is based on the object of further developing a device of the kind mentioned in the introduction in such a manner that it allows the use of multiple syringes and can be produced inexpensively while ensuring an improved handling by patients.

Another object of the invention is to allow a repeated use of the device and an accurate metering of any dispensed quantities.

These objects are attained by a device which is configured to receive and dispense a multiple syringe or cartridge, includes a handling portion for receiving the pressure medium, the dispensing piston, and the guide portion provided with a receiving flange for the multiple syringe, and comprises locking means that are releasable by applying manual pressure to the handling portion and are arranged on the handling portion and operatively connected to locking means provided on the dispensing piston.

Further preferred embodiments of the invention are defined in the dependent claims.

BRIEF DESCRIPTION OF THE DRAWINGS

The invention will be explained in more detail hereinafter with reference to drawings of exemplary embodiments, where:

FIG. 1 shows an exploded view of a first exemplary embodiment of a device according to the invention for automated dispensing of a double syringe;

FIG. 1d shows a perspective view of the assembled device according to FIG. 1;

FIG. 2 shows a perspective view of a part of the device shown in FIG. 1 with the dispensing piston in the tensioned position;

FIG. 3 shows a perspective view of the dispensing piston of FIG. 1;

FIG. 4 shows a partly sectioned view according to plane IV-IV in FIG. 2 illustrating the locked position of the dispensing piston in the tensioned piston position;

FIG. 5 shows a partly sectioned view according to plane V-V in FIG. 2 illustrating the released position of the locking sleeve;

DETAILED DESCRIPTION OF THE INVENTION

Figure 1A:
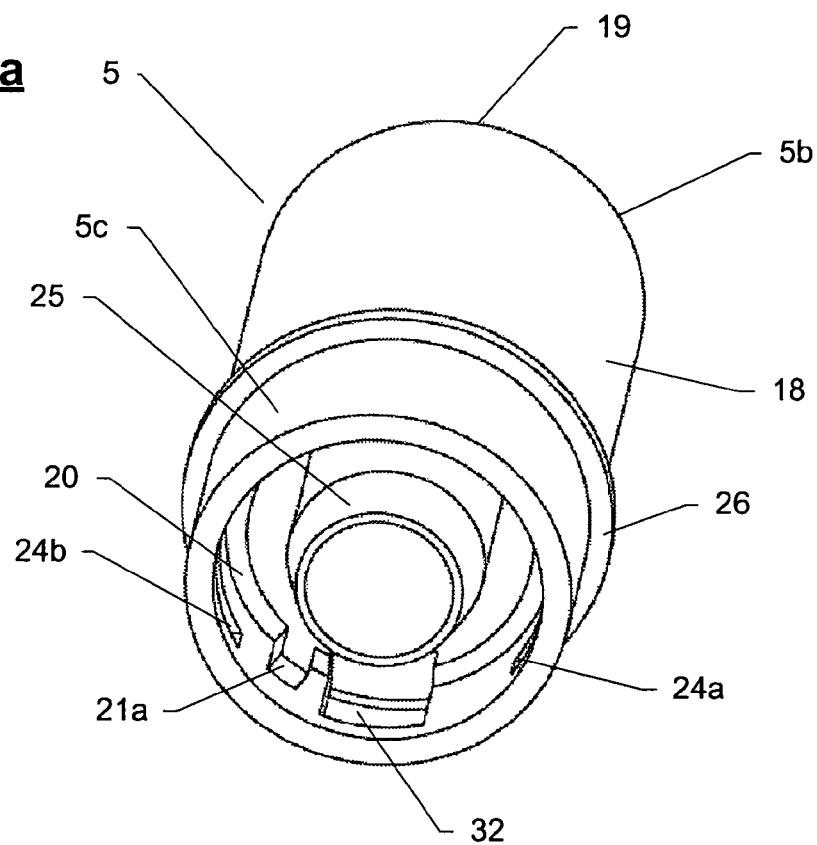
FIG. 1a shows a perspective view of the handling portion of the device shown in FIG. 1.

Hereinafter, in the exemplary embodiments, double syringes are depicted and described, but multiple syringes or multiple cartridges having more than two storage containers are also encompassed, in which case the dispensing piston is adapted accordingly. The terms "front" and "rear" refer to the syringe outlet, which is on the front side.

FIG. 1 shows a first embodiment of a dispensing device 1 according to the invention for a double syringe, comprising a dispensing piston 2, a guide portion 3, a spring element 4 that serves as the pressure medium, a handling portion 5, and a locking sleeve 6.

Dispensing piston 2 according to FIGS. 1 and 3 has the form of a hollow cylinder 8 that is closed at its front end 2a by a plunger support 9 and open at its rear end 2b. At the front end 2a of the external circumferential surface of dispensing piston 2, a finger rest 7 is provided whose underside extends along a part of the circumference of hollow cylinder 8 and whose plane upper side extends essentially perpendicularly to the circumferential surface of hollow cylinder 8. Finger rest 7 is insertable in a receiving slot 10 of hollow cylinder 8 and attachable therein, as appears in FIG. 1 and will be described in more detail in the following description. Along the underside of dispensing piston 2, a serrated locking toothing 35 is provided. Locking toothing 35 extends over a distance that corresponds to the total stroke of the dispensing piston. In the illustrated position of dispensing piston 2, the foremost tooth space 35a of the locking toothing is located in the axial area of locking catch 30. The inner side of locking catch 30 has a shape that is equivalent to that of the spaces of the toothing, thereby allowing a positive engagement of locking catch 30 in any one of toothing spaces 35.

As appears in FIG. 1, guide portion 3 essentially consists of a hollow cylinder 12 whose open end 3b is adapted to receive dispensing piston 2. On the upper side of its circumferential surface, hollow cylinder 12 is provided with an opening 13 that extends over a large part of guide portion 3 longitudinally and whose width essentially corresponds to the attachment area of finger rest 7 on dispensing piston 2 and which further serves for receiving double plunger 55. In this manner, an axial movement of dispensing piston 2 within guide portion 3 is possible while finger rest 7 protrudes from opening 13. A forward stop shoulder 34 for locking sleeve 6 is defined by the width of the transversal wall portion along a part of the external circumference of guide portion 3.

The piston movement within guide portion 3 is limited by a receiving flange for syringe 15 at front end 3a of guide portion 3. This receiving flange for syringe 15 is in the form of a transversal wall that extends beyond the cylinder diameter on both sides and has a U-shaped recess in its central area in which a double syringe 50 and its double plunger 55 are insertable. On the upper edge of location flange 15, an insertion opening 16 for the syringe flange of a double syringe is provided, as appears in FIG. 1. Thus, during the actuation of double plunger 55, the forward end position of dispensing piston 2 inside guide portion 3 is attained at the end position point of the double plunger inside the double syringe.

Spring element 4 is formed of a cylindrically coiled compression spring whose front end 4a is arranged in the interior of hollow cylinder 8 in such a manner that its rear end 4b protrudes from the open rear end 2b of dispensing piston 2.

FIG. 1d illustrates an assembled device according to the invention with a double syringe 50 and a mixer 53. The double syringe is actuated by means of a double plunger 55 and further comprises a retaining flange 54 and a thrust plate 57.

According to FIG. 1a, handling portion 5 also has an essentially cylindrical shape 18 whose front end 5a is open and whose rear end 5b is closed by an end wall 19. In the forward section, the hollow interior of handling portion 5 widens from a stop collar 20 that extends circumferentially along the inner wall.

Stepped stop collar 20 defines a forward receiving section 33 of handling portion 5 that is configured to receive rearward end section 3c of guide portion 3 such that its rear end 3b abuts against stepped stop collar 20. On two opposed sides of the inner wall of receiving section 33, respective positioning cams 21a, b are arranged which extend in the forward direction from stepped stop collar 20.

Accordingly, in the rearward end section 3c of guide portion 3, two corresponding positioning slots 22a, b are provided, thereby ensuring the correct orientation of guide portion 3 during its insertion into handling portion 5. On two opposed sides of guide portion 3, respective snap noses 23a, b are arranged on the surface of rearward end section 3c. Corresponding snap grooves 24a, b are provided along the inner wall of receiving section 33. In this manner, the assembly of components 3, 5 establishes a non-detachable snap connection between snap noses 23a, b and snap grooves 24a, b.

A cylindrical spring guide 25 is arranged in the central area of the hollow interior of handling portion 5 which essentially extends over its entire length in the axial direction and internally connects to end wall 19. More specifically, the external diameter of cylindrical spring guide 25 essentially corresponds to the internal diameter of spring element 4. In this manner, cylindrical spring guide 25 guides rear end 4b of spring element 4 toward the inner side of end wall 19, whereby spring element 4 is compressed during the assembly of components 2, 3, 4, and 5.

A rearward stop shoulder 26 is arranged along cylindrical surface 18 and circumferentially projects behind receiving section 33. Specifically, the stop shoulder is located at the front end of end section 5c of handling portion 5.

Figure 1B:
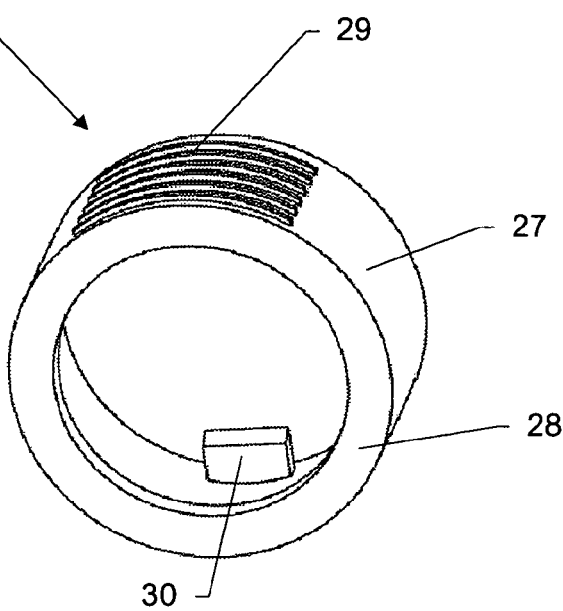
FIG. 1b shows a perspective view of the locking sleeve of the device shown in FIG. 1.
Figure 1C:
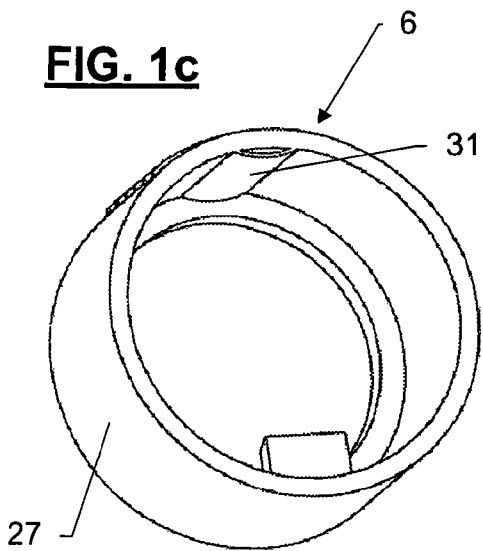
FIG. 1c shows a different perspective view of the locking sleeve of FIG. 1b.

According to FIGS. 1b and 1c, locking sleeve 6 has an annular sleeve envelope 27 that is slidable over forward end section 5c of handling portion 5. Furthermore, as compared to the external diameter of end section 5c, a slightly oval internal diameter of sleeve envelope 27 is provided whose largest dimension is located between the locking catch and the finger rest and allows a corresponding displacement. After its assembly, forward front face 28 of locking sleeve 6 rests against forward stop shoulder 34 of guide portion 3. In this position, rear end 6b of locking sleeve 6 abuts against rearward stop shoulder 26 of handling portion 5.

Along the inner wall of sleeve envelope 27, a locking catch 30 is arranged which extends radially inwards. A lateral aperture 32 that corresponds to locking catch 30 is provided in the forward end section 5c of handling portion 5. Due to the elliptical shape of the internal dimension of the locking sleeve and cylindrical surface 5c, it is possible to move locking catch 30 toward lateral aperture 32 during the assembly of components 5, 6 and subsequently engage locking catch 30 in lateral aperture 32 so that locking catch 30 projects into the hollow interior of handling portion 5.

According to FIG. 1c, an elastic pressure element 31 is arranged on the side of the inner wall of sleeve envelope 27 opposite locking catch 30. Pressure element 31 causes a force to be applied to locking sleeve 6 in the opposite direction with respect to locking catch 30 in order to bring the latter into engagement with the locking toothing. On the outside of the sleeve, a finger rest 29 is associated to elastic pressure element 31. By applying pressure to this finger rest, pressure element 31 and thus locking sleeve 6 along with locking catch 30 are disengaged within their radial play from locking toothing 35 on the underside of dispensing piston 2, thereby releasing the dispensing piston.

In FIGS. 4 and 5, dispensing device 1 is shown in a sectioned view according to planes IV-IV and V-V in FIG. 2. In the closed position of locking sleeve 6 shown in FIG. 4, finger rest 29 is under the impact of the pressure element and thus, within its radial play, in the remote position from the forward end section 5c of handling portion 5. In this position, the inner side of locking catch 30 extends through aperture 32 into the interior of handling portion 5. Therefore, locking catch 30 engages in one tooth space of the locking toothing 35 of dispensing piston 2 extending along the inner wall of handling portion 5. In the rearward end position of dispensing piston 2 shown here, locking catch 30 engages in forward tooth space 35a. By the thus formed locking means, dispensing piston 2 is retained in its axial position with respect to handling portion 5 and against the force applied thereto by spring element 4.

In the releasing position of locking sleeve 6 shown in FIG. 5, finger rest 29 is in a position that results from applying a manual pressure, in which it is displaced with respect to forward end section 5c of handling portion 5 within its predetermined play. The serrated inner side of locking catch 30 is thus withdrawn from the interior of handling portion 5, thereby releasing the locking means.

When the manual pressure applied to finger rest 29 is cancelled, locking sleeve 6 is returned to the closed position shown in FIG. 4 by the spring action of pressure element 31. This causes an engagement thereof in the closest tooth space. Consequently, locking toothing 35 allows dispensing piston 2 to catch with handling portion 5 in different piston positions according to the requirements.

Manually returning dispensing piston 2 rearwardly is possible from any piston position by applying pressure to finger rest surface 11 of finger rest 7 for the wedge-shaped configuration of locking catch 30 and of locking toothing 35, respectively, allows a rearward disengagement of locking catch 30 from a tooth space.

Figure 6:
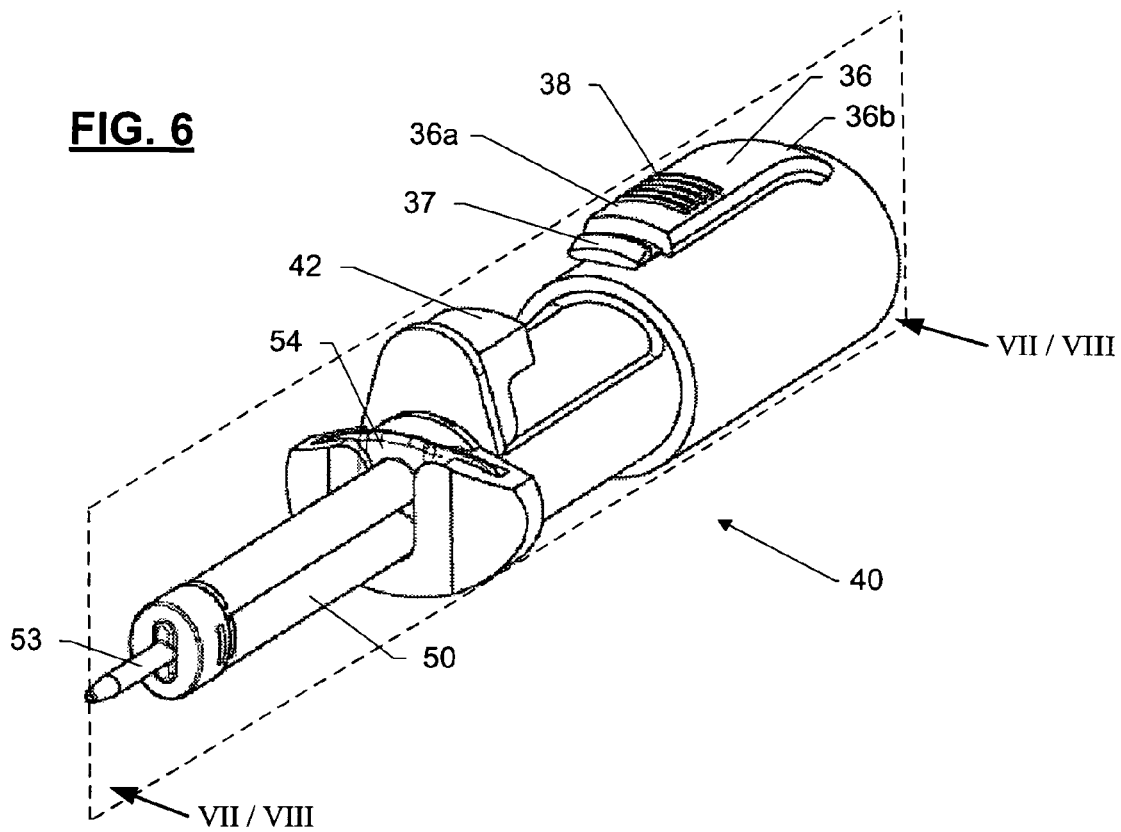
FIG. 6 shows a perspective view of a second exemplary embodiment of a device according to the invention with a double syringe for automated dispensing.

FIG. 6 shows a second exemplary embodiment of a dispensing device 40 according to the invention in a perspective view. Those features which correspond to the first exemplary embodiment are designated by the same reference numerals. Further shown is a double syringe 50 that is suitable for use with dispensing device 1, 40.

This variant essentially corresponds to the first exemplary embodiment while the main difference consists in a simplified locking and releasing mechanism and the dispensing operation cannot be interrupted.

Device 40 comprises an elastic finger rest 36 whose rear end 36b is rigidly connected to handling portion 5 in the area of its rear end 5b and extends forwardly along cylindrical surface 18 up to front end 5a of handling portion 5. At the front end 36a of finger rest 36, a locking catch 37 is arranged. Here, the finger rest with the locking catch essentially has the function of locking sleeve 6 in the first embodiment 1 of the dispensing device. In this embodiment, in contrast to the first exemplary embodiment, locking catch 37 is directed outwardly.

A locking notch 41 that corresponds to locking catch 37 is provided on dispensing piston 2. At its front end, dispensing piston 2 has a location slot 10 in which finger rest 7 is insertable. The finger rest has a locking support 42 that extends above hollow cylinder 8 of dispensing piston 2 in the shape of an umbrella. On the underside of locking support 42, locking notch 41 is arranged, see FIG. 7.

When pressure is applied to pressure surface 38 of finger rest 36, locking catch 37 is depressed and disengages from locking notch 41. Due to the spring arm configuration of finger rest 36, locking catch 37 is returned to its initial position when the manually applied pressure is cancelled while the wedge shape of locking catch 37 ensures its engagement in the rearward position when the appliance is reused at a later time.

Figure 7:
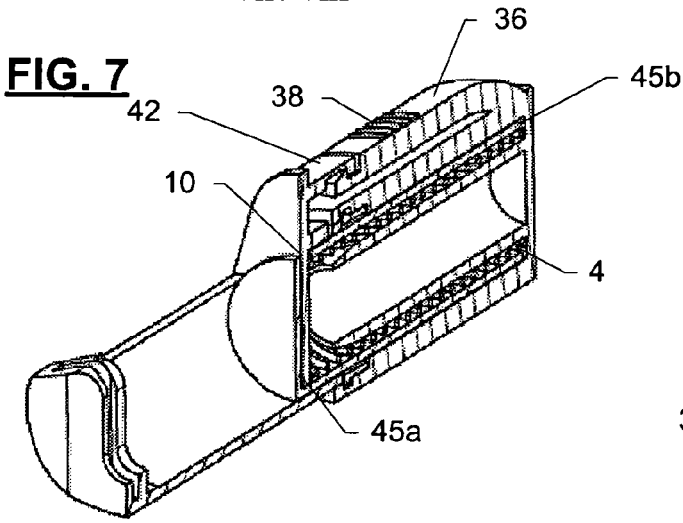
FIG. 7 shows a section according to plane VII-VII in FIG. 6 in a tensioned position of the dispensing piston.
Figure 8:
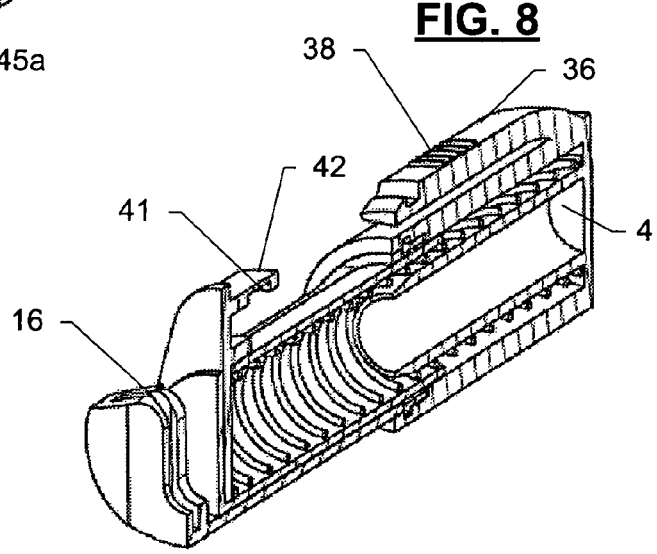
FIG. 8 shows a section according to plane VIII-VIII in FIG. 6 in a released position of the dispensing piston.

FIGS. 7 and 8 show sectioned perspective views of guide portion 2 according to section planes VII-VII and VIII-VIII in FIG. 6 in the tensioned and released positions.

From the description of the exemplary embodiments, various modifications are accessible to those skilled in the art without departing from the protective scope of the invention, which is defined by the claims. Thus, a locking toothing may also be provided with external locking means according to the second exemplary embodiment. In this manner, by simply canceling the manually applied pressure, it is possible to lock the dispensing piston in a locking means at any time during dispensing. Furthermore, locking means may be provided which comprise a locking catch on dispensing piston 2 and a locking toothing on handling portion 5. It is further possible to provide an external locking means in the form of a locking catch on a locking sleeve or an internal locking means in the form of a locking bracket on the handling portion. Also, instead of a compression spring, a compressed air cartridge or other such pressure medium may be used as a pressure medium to facilitate self-dispensing.

What is claimed is:

1. A device, which is configured to receive and dispense a multiple syringe or cartridge, comprising:
    a dispensing piston, actuatable by a pressure medium, configured to dispense the multiple syringe;
    a guide portion that displaceably supports the dispensing piston and includes a receiving flange that is configured to receive a retaining flange of the multiple syringe;
    a handling portion configured to receive the pressure medium, the dispensing piston, and the guide portion; and
    first and second locking elements,
    wherein the first locking elements are releasable by applying manual pressure to the handling portion, are included in the handling portion, and are operatively connected to the second locking elements of the dispensing piston,
    wherein the first locking elements include a locking catch on an outlet side end of the handling portion, and
    wherein the second locking elements include at least one locking toothing on the dispensing piston that cooperates with the locking catch.

2. The device of claim 1, wherein the pressure medium comprises a spring element configured to fit in an interior of the dispensing piston and to project from the interior of the dispensing piston.

3. The device of claim 1, wherein the dispensing piston includes a plurality of locking toothings.

4. The device of claim 1, wherein the first locking elements further include a locking sleeve on an outlet side end of the handling portion, and wherein the locking catch is on an interior of the handling portion.

5. The device of claim 4, wherein an inner area of the locking sleeve opposite the locking catch includes an elastic pressure element configured to push the locking catch into a tooth space of the locking toothing such that the first locking elements are releasable by applying manual pressure to an outside of the inner area of the locking sleeve opposite the locking catch.

6. A device, which is configured to receive and dispense a multiple syringe or cartridge, comprising:
    a dispensing piston, actuatable by a pressure medium, configured to dispense the multiple syringe;
    a guide portion that displaceably supports the dispensing piston and includes a receiving flange that is configured to receive a retaining flange of the multiple syringe;
    a handling portion configured to receive the pressure medium, the dispensing piston, and the guide portion; and
    first and second locking elements,
    wherein the first locking elements are releasable by applying manual pressure to the handling portion, are included in the handling portion, and are operatively connected to the second locking elements of the dispensing piston, and
    wherein the first locking elements are at an end of an elastic locking support extending in a longitudinal direction of the dispensing piston.

7. The device of claim 1, wherein an outlet side end of the dispensing piston includes a finger rest configured to manually transfer the dispensing piston from a forward position to a rearward position.

8. The device of claim 1, wherein an interior of the handling portion includes an essentially cylindrically shaped and axially extending spring guide.

9. The device of claim 1, wherein a rear end section of the guide portion includes at least two opposed positioning slots and wherein an inner wall of the handling portion includes corresponding positioning cams.

10. The device of claim 1, wherein the receiving flange, provided at an outlet side end of the guide portion, is coded for the multiple syringe or cartridge for affixing the multiple syringe or cartridge in a directional manner.

11. An arrangement for the application of medical preparations, comprising a device according to claim 1 and by a multiple syringe that is insertable into the device.

12. The device of claim 1, wherein the receiving flange includes an insertion opening that receives the retaining flange.

13. The device of claim 1, wherein a front end of the dispensing piston is closed by a plunger support and a rear end of the dispensing piston is open.

14. The device of claim 1, wherein the at least one locking toothing is on an underside of the dispensing piston.

15. The device of claim 9, wherein the positioning cams are on opposing sides of the inner wall of the handling portion.

* * * * *